United States Patent [19]

Robinette-Lehman

[11] Patent Number: 4,635,635
[45] Date of Patent: Jan. 13, 1987

[54] TOURNIQUET CUFF

[75] Inventor: Cynthia Robinette-Lehman, Larkspur, Colo.

[73] Assignee: Aspen Laboratories, Inc., Englewood, Colo.

[21] Appl. No.: 676,321

[22] Filed: Nov. 29, 1984

[51] Int. Cl.$^4$ ............................................. A61B 17/12
[52] U.S. Cl. ................................................. 128/327
[58] Field of Search ....................... 128/327, 686, 677

[56] References Cited

U.S. PATENT DOCUMENTS

| | | | |
|---|---|---|---|
| 800,467 | 9/1905 | Myers | 128/327 |
| 814,795 | 3/1906 | Myers | 128/327 |
| 3,467,077 | 9/1969 | Cohen | 128/327 |
| 3,504,675 | 11/1970 | Bishop, Jr. | 128/327 |
| 3,633,567 | 1/1972 | Sarnoff | 128/2.05 |
| 3,654,931 | 7/1972 | Hazlewood | 128/327 |
| 3,669,096 | 6/1972 | Hurwitz | 128/327 |
| 3,670,735 | 6/1972 | Hazlewood | 128/327 |
| 3,713,446 | 1/1973 | Sarnoff | 128/327 |
| 3,906,937 | 9/1975 | Aronson | 128/327 |
| 3,930,506 | 6/1976 | Overend | 128/325 |
| 3,968,788 | 7/1976 | Hopkins | 128/327 |
| 3,977,393 | 8/1976 | Kovacic | 128/327 |
| 4,106,499 | 8/1978 | Ueda | 128/327 |
| 4,149,540 | 4/1979 | Hasslinger | 128/327 |
| 4,177,813 | 12/1979 | Miller et al. | 128/326 |
| 4,354,503 | 10/1982 | Golden | 128/327 |
| 4,406,281 | 9/1983 | Hubbard et al. | 128/132 |
| 4,465,076 | 8/1984 | Sturgeon | 128/686 |

Primary Examiner—Robert Peshock
Assistant Examiner—J. Hakomaki
Attorney, Agent, or Firm—Paul David Schoenle

[57] ABSTRACT

This invention relates to an improved tourniquet cuff. The cuff is of the type which includes an inflatable member for wrapping about a body part, such that the inflatable member is secured to the body part, and at least one tube is provided to facilitate inflation of the inflatable member, with the inflatable member having a length dimension, and a width dimension. The inflatable member is formed in a substantially arcuate shape, with the radius of the arc passing along the width dimension. In the preferred embodiment, the inflatable member includes a bladder and a polyester reinforced backing, both of which have the arcuate shape. The invention also provides a set of tourniquet cuffs having the arcuate shape and in which the cuffs of the set nest one within the other. In the preferred embodiment, the inside radius of one cuff is equal to the outside radius of the next smaller size cuff.

6 Claims, 4 Drawing Figures

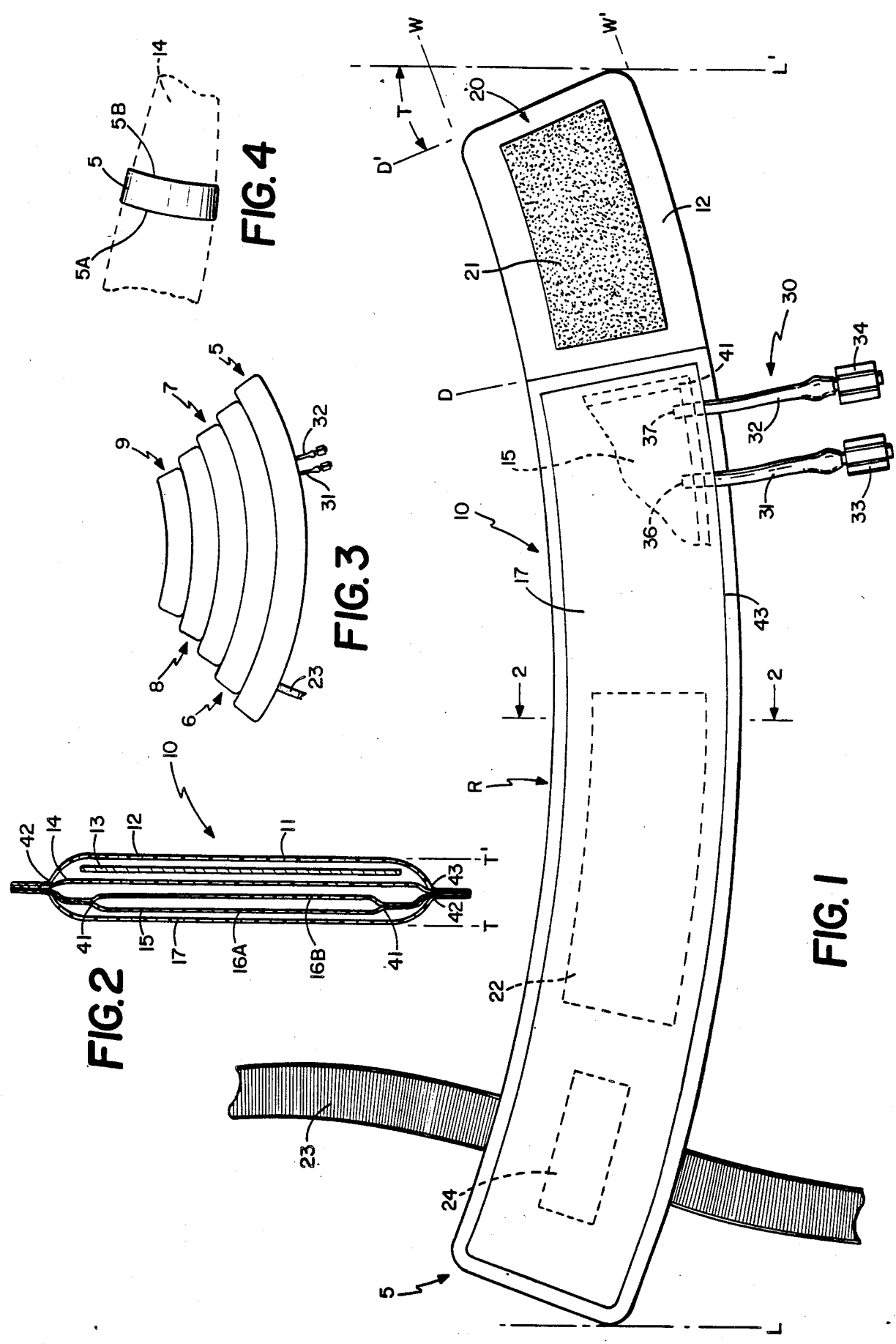

TOURNIQUET CUFF

BACKGROUND OF THE INVENTION

1. Field of the Invention.

The invention in general relates to tourniquets of the type which are wrapped around a body member and are inflated to provide pressure for controlling blood flow.

2. Description of the Prior Art.

U.S. Pat. Nos. 3,504,675 issued to W. A. Bishop, Jr. and 3,670,735 issued to Lewis F. Hazlewood are examples of known inflatable tourniquets. Both of these tourniquets are disposable, as is the particular embodiment of a tourniquet which shall be described in the present application.

The prior art tourniquets have been known to produce irregular pressures over the surface of the tourniquets which are applied to the limbs. In particular, the prior art tourniquets often produce greater pressures at the side of the tourniquet that is nearest the distal end of the limb to which is it applied than on the side of the tourniquet which is nearest the proximal end of the limb to which it is applied. Herein, proximal means the end closest to the trunk of the body and distal means the side closest to the end of the limb.

Another disadvantage of prior art tourniquets is that application of the tourniquets to the limb is hindered by the fact that these tourniquets sometimes do not conform well to the shape of the limb to which they are applied.

Other problems that have occurred with prior art tourniquets are stretching or growth of a tourniquet cuff during inflation, and ballooning or the rubber-band effect which cause concentrated pressures at the center of the cuff to limb interface, and which can result in excessive cuff inflation times.

SUMMARY OF THE INVENTION

The object of the present invention is to provide a tourniquet cuff which overcomes one or more disadvantages of the prior art tourniquet cuffs. It is a further object of the invention to provide such a tourniquet cuff which is also inexpensive to manufacture and thus may be used once and then disposed of.

It is a further object of the invention to provide a set of tourniquet cuffs which are capable of conforming to an unusually wide variety of limb sizes.

The invention provides a tourniquet cuff which includes an inflatable member, a means for securing the inflatable member about a body part, and a means for facilitating inflation of the inflatable member; the inflatable member has a length dimension for wrapping around the body part, a thickness dimension for placement perpendicular to the surface of the body part, and a width dimension for spanning the body part, and the member is formed in a substantially arcuate shape with the radius of the arc passing along the width dimension. Preferably, the inflatable member includes a backing material and a bladder, and both the bladder and the backing material are formed in an arcuate shape.

The invention also provides an improved set of tourniquet cuffs of the type just described. The set includes a plurality of sizes of the cuffs, with the sizes configured so that the arcs of the cuffs nest within one another.

The design of the cuff results in the cuff taking a shape which is substantially a frustum of a cone when it is wrapped about a body part. It has been found that this conical shape more nearly approximates the shape of the areas of the limbs about which tourniquets are traditionally placed.

It has been found that the conformance of the set of cuffs according to the invention to most sizes and shapes of body limbs is outstanding.

It has been found that the improved conformance results in a more even pressure distribution to the limb. It has all but eliminated the pressure differences generally found between the distal and proximal end on most prior art cuffs.

It has also been found that the cuff according to the invention occludes blood flow at lower pressure settings than prior art cuffs, and further reduces the average cuff inflation time.

Numerous other aspects, features, objects, and advantages of the invention will now become apparent from the following detailed description when read in conjunction with the accompanying drawings, in which:

BRIEF DESCRIPTION OF THE DRAWINGS

FIG. 1 is an elevational view of a tourniquet cuff according to the invention looking down on the side that is intended to be applied against a body surface;

FIG. 2 is a cross-sectional view taken through line 2—2 of FIG. 1;

FIG. 3 is diagrammatic illustration showing the nesting of one embodiment of a set of cuffs according to the invention; and FIG. 4 is a diagrammatic illustration of a cuff according to the invention wrapped around a human limb.

DESCRIPTION OF THE PREFERRED EMBODIMENT

Referring to FIG. 1, a tourniquet cuff according to the preferred embodiment of the invention is shown. The cuff 5 includes an inflatable member 10, a means 20 for securing the inflatable member around a body part, and a means 30 for facilitating inflation of the inflatable member 10. The inflatable member 10 has a length dimension L—L', a thickness dimension, which is perpendicular to the plane of the drawing of FIG. 1, and a width dimension W—W'. According to the invention, the inflatable member 10 has a substantially arcuate shape with a radius R of the arc passing along the width dimension. Note that in FIG. 1 R is not the full radius of the arc but is only intended to show the direction of a radius.

Turning now to a more detailed description of the preferred embodiment of the invention, we refer to FIGS. 1 and 2. In the preferred embodiment, inflatable member 10 includes a flexible backing 12, 14 and a stiffener 13. Stiffener 13 is positioned between the two pieces 12 and 14 of backing material and the edges of the backing material are sealed, as at 42, to form an envelope containing stiffener 13. The preferred embodiment of inflatable member 10 also includes a bladder 15 and a bladder protective layer 17. Bladder 15 is preferably formed of two sheets 16A and 16B which are sealed along their edges. Protective layer 17 is placed over bladder 15 and both are sealed to the envelope formed by backing pieces 12 and 14 so that bladder 15 is enclosed in an envelope formed by piece 14 and protective layer 17. It is noted that the thicknesses of the elements 12, 13, 14, 15, and 17 making up the inflatable member and the relative distance between these pieces has been exaggerated in FIG. 2 in order to more clearly show the individual pieces and the relationships between the pieces. Thus the thickness T—T' is not to be taken to indicate the true thickness of the uninflated inflatable member as compared to the width W—W' and length L—L'. In an actual cuff, the thickness T—T' would be substantially less as compared to the width and length.

Turning now to a detailed description of the preferred embodiment of the means 20 for securing the inflatable member 10 to a body part, we return to FIG. 1. The preferred embodiment of means 20 includes a fabric hook and loop fastener system 21 and 22 and a ribbon 23 which is attached to backing 12 by attachment strip 24. In the embodiment shown, 21 comprises an adhesive-backed strip of fabric hooks, with the adhesive surface applied to the upper surface (the surface facing out of the paper) of backing 12. Adhesive-backed strip 22 of fabric loops is attached to the lower surface of backing material 12. In the drawing the strip 22 is shown in dotted outline since it is on the reverse side of the strip 12 and would not be seen in the view. Ribbon 23 and attachment strip 24 form a secondary means for securing the cuff. Ribbon 23 is placed against the back side of backing 12 and strip 24 is placed over the ribbon and sealed to backing 12 to attach the ribbon 23 to backing 12. Again, strip 24 is dotted to indicate that it is on the reverse side of the backing 12 and would not be visible from the front side.

Turning now to a detailed description of the means 30 for facilitating the inflation of inflatable member 10, means 30 includes tubing 31 and 32 which extend under the edge of protective layer 17 and through the seal 41 of the two sheets 16a and 16b forming bladder 15. A corner of bladder 15 is shown in dotted outline in FIG. 1 to indicate the connection of tubes 31 and 32. The ends 36 and 37 of tubes 31 and 32 within bladder 15 are open. The opposite ends of tubes 31 and 32 are connected to male connectors 33 and 34 for connecting to an inflation and deflation means (not shown). In the preferred embodiment shown, one of the tubes 31 and 32 is intended to be connected to a source of pressurized gas, while the other one of the tubes is connected to a deflation valve. In other embodiments, there is only one tube which is used for both inflation and deflation.

Turning now to a description of materials out of which the preferred embodiment is made, the inner and outer layers 12 and 14 of the backing envelope 11 and the attachment strip 24 are preferably made of a lamination of B. F. Goodrich KOROSEAL TM reinforced with polyester fabric. The material used is a lamination known under the trademark Weblon. The preferred fabric weight is 12 oz. per square yard, with a grab tensile strength of 120×120 pounds per inch, and a tear strength of 24×24 pounds. The polyester preferably has a yarn count of 24×24 and a Denier of 220. The total vinyl thickness is preferably 10 mil. Stiffener 13 is preferably made of 0.030 inch polypropylene sheeting, medical grade. The bladder sheets 16A and 16B and the protective layer 17 are preferably made of 0.012 mil. translucent PVC (poly vinyl chloride). The hook and loop fastener system 21 and 22 is preferably made of adhesive-backed VELCRO hook and loop fabric. Tubing 31 and 32 is preferably 3/16" O.D.×⅛" I.D. clear medical grade tubing made of a material such as PVC, silicone rubber, etc. Connectors 33 and 34 are preferably white nylon, male, Luer-compatible connectors.

FIG. 4 shows a diagram of a cuff such as cuff 5 of FIG. 1 when it is wrapped around a human limb 4, such as an arm or a leg. As shown, when the cuff 5 is wrapped in a circle about the limb 4, it forms a frustum of a cone. This conical shape of the cuff 5 as applied conforms to the general conical nature of limbs 4. In the preferred embodiment, the proximal end 5A and the distal end 5B of cuff 5 are indicated in order to ensure proper placement of the cuff 5 on limb 4.

The incorporation of a polyester reinforcement in the cuff layers eliminates the possibility of stretch or growth of the backing envelope 11 during inflation. The elimination of stretching further adds to the ability of the cuff to occlude blood at lower pressure setting.

The stiffening layer 13 as well as the polyester reinforcement in the PVC force the "growth" of the bladder during inflation to occur only in the direction of the limb. This further eliminates the "ballooning" or "rubber band" effect which cause concentration of pressures at the center of the cuff-to-limb interface. The stiffener 13 further prevents rolling of the cuff along the limb in the distal direction. This feature also decreases the cuff inflation time. On the other hand, because of the strength and stiffness of backing envelope 11 and stiffener 13, the bladder 15 and protective layer 17 may be made out of relatively soft material, which prevents tissue damage during inflation.

It has been found that the protective layer 17 also helps to eliminate ballooning and protects bladder growth at extremely high pressures.

Another feature of the invention is that all the materials used in the cuff are water or solution repelling and thus there is very little danger of the cuff harboring and absorbing chemicals and solutions that might cause skin-side burns and irritation.

Turning now to FIG. 3, a set of cuffs 5 through 9 according to the invention is shown. By measuring the arms and legs of a large number of people, a preferred set of sizes of cuffs according to the invention required to conform to as many limb sizes as possible, was determined. It was discovered that by nesting the various sizes, it was possible to provide a set of cuffs which fit nearly every conceivable limb size. By nesting it is meant that the radius of the arc of a smaller size cuff is smaller than the radius of the arc of a larger size cuff. That is, of the cuffs shown in FIG. 3, the arc of cuff 5 would have the largest radius, while the arc of cuff 9 would have the smallest radius, and intermediate cuffs 6, 7, and 8 would have intermediate radii. In FIG. 3 ribbon 23 and tubing 31 and 32 are shown for cuff 5 in order to orient the drawing, but other details of cuff 5 and the details of cuff 6 through 9 are not shown. In the preferred embodiment of the invention the inside radius of one size cuff corresponds to the outside radius of another size cuff. This arrangement has been found to conform well to various limb tapers, however it is not necessary. The principles of the invention may be utilized by making, say, the inside radius of a smaller size cuff smaller than the inside radius of a larger size cuff, or for example, the mean radius of a smaller size cuff smaller than the mean radius of a larger size cuff.

The following table indicates the preferred dimensions for the embodiment of the set of cuffs described.

| BLADDER LENGTH | W-W' (CUFF WIDTH) | T (° OF TAPER) | R (INSIDE RADIUS) | D-D' (ADHESIVE AREA) | L-L' (OVERALL LENGTH) |
|---|---|---|---|---|---|
| 8 | 2⅜ | 17° | 20.8 | 3.4 | 12.5 |
| 12 | 3 | 22° | 23.8 | 3.4 | 16.0 |
| 18 | 4 | 26° | 27.8 | 4.8 | 23.3 |
| 24 | 4 | 27° | 31.8 | 5.4 | 29.4 |
| 34 | 4 | 32° | 35.8 | 6.0 | 39.2 |

All dimensions are given in inches except the degree of taper which is given in degrees.

The various sealed joints, such as 41, 42, 43, and the attachment of strip 24 to backing material 12 are made by radio frequency (RF) sealing.

A novel tourniquet cuff that provides more even pressure distribution to the limb and numerous other features and advantages as compared to prior art cuffs has been described. While the above description of the invention has been referenced to a few particular embodiments, it is evident that, now that the advantages of an arcuate cuff shape and the nesting of a set of cuffs has been disclosed, those skilled in the art can now make numerous uses of, modifications of, and departures from the specific embodiments described herein without departing from the inventive concepts. For example, one or another of the various parts of the preferred cuff, such as the stiffener 13 or the protective layer 17, may be eliminated. Other means may be used for securing to the body, or other means for facilitating inflation may be incorporated. A wide variety of cuff dimensions may be used. Consequently, the invention is to be construed as embracing each and every novel feature and novel combination of features within the appended claims.

What I claim is:

1. An improved tourniquet cuff of the type including an inflatable member, a means for securing said inflatable member around a body part, and a means for facilitating inflation of said inflatable member, said member having a length dimension for wrapping around said body part, a thickness dimension for placement perpendicular to the surface of said body part, and a width dimension for spanning a portion of said body part, said member having a substantially arcuate shape with the radius of the arc passing along said width dimension, at least three layer elements coupled at their ends to define a pair of cavities, a stiffener in one cavity, said inflatable member being disposed in the other cavity whereby a middle layer element for said three layer elements separates said stiffener from said inflatable member, said inflatable member further comprising a pair of sheets sealingly coupled together within said other cavity to define a first seal for said inflatable member, and said pair of sheets extending from said first seal to also sealingly engage said middle layer element and define a second seal for said inflatable member.

2. An improved tourniquet cuff as in claim 1 wherein an outer layer element adjacent said stiffener is less flexible than an outer layer element adjacent said inflatable member.

3. An improvde tourniquet cuff as in claim 1 wherein said inflatable member forms an opening to receive pressurized fluid, said opening defining a width dimension which is less than a width dimension for said stiffener.

4. An improved set of tourniquet cuffs of the type including an inflatable member, a means for securing said inflatable member about a body part, and means for facilitating inflation of said inflatable member, said inflatable member having a length dimension for wrapping around said body part, a thickness dimension for placement perpendicular to the surface of said body part, and a width dimension for spanning said body part, wherein the improvement comprises: said inflatable member of each of said cuffs in said set having a substantially arcuate shape with the radius of the arc passing along said width dimension.

5. A set of tourniquet cuffs as in claim 4 wherein said set includes a plurality of sizes of said cuffs, with the arc of one cuff nesting within the arc of another cuff.

6. A set of tourniquet cuffs as in claim 5 wherein the inside radius of one cuff is equal to the outside radius of the next smaller size cuff.

* * * * *